United States Patent
Yu et al.

(10) Patent No.: US 8,788,017 B2
(45) Date of Patent: Jul. 22, 2014

(54) METHOD AND EQUIPMENT FOR IMAGE-GUIDED STEREOTACTIC RADIOSURGERY OF BREAST CANCER

(75) Inventors: Xinsheng Cedric Yu, Clarksville, MD (US); Ying Su Yu, Clarksville, MD (US); William Regine, Cockeysville, MD (US)

(73) Assignees: University of Maryland, Baltimore, Baltimore, MD (US); Xcision Medical Systems, LLC, Clarksville, MD (US)

( * ) Notice: Subject to any disclaimer, the term of this patent is extended or adjusted under 35 U.S.C. 154(b) by 900 days.

(21) Appl. No.: 12/449,827

(22) PCT Filed: Feb. 26, 2008

(86) PCT No.: PCT/US2008/055043
§ 371 (c)(1),
(2), (4) Date: Sep. 15, 2009

(87) PCT Pub. No.: WO2008/106468
PCT Pub. Date: Sep. 4, 2008

(65) Prior Publication Data
US 2010/0094119 A1    Apr. 15, 2010

Related U.S. Application Data

(60) Provisional application No. 60/904,037, filed on Feb. 28, 2007.

(51) Int. Cl.
*A61B 5/05* (2006.01)
*A61B 6/00* (2006.01)
*A61B 6/02* (2006.01)
*A61B 6/04* (2006.01)

(52) U.S. Cl.
CPC ... *A61B 6/00* (2013.01); *A61B 6/02* (2013.01); *A61B 6/022* (2013.01); *A61B 6/0435* (2013.01)

USPC ........... 600/411; 600/407; 600/410; 600/415; 600/421; 600/436; 378/41; 378/51; 378/64; 378/65

(58) Field of Classification Search
CPC ............ A61B 6/00; A61B 6/02; A61B 6/022; A61B 6/0435
USPC ................. 600/407, 410, 411, 415, 421, 436; 378/41, 51, 64, 65
See application file for complete search history.

(56) References Cited

U.S. PATENT DOCUMENTS 5,451,789 A * 9/1995 Wong et al. .............. 250/363.03
5,537,452 A * 7/1996 Shepherd et al. ............... 378/65
(Continued)

FOREIGN PATENT DOCUMENTS

KR    1019990041734 A    6/1999
WO    2006/088886 A2    8/2006

OTHER PUBLICATIONS

"MR Imaging-guided Focused US Ablation of Breast Cancer: Histopathologic Assessment of Effectiveness—Initial Experience1" by Gianfelice et al, Radiology, 227, pp. 849-855, 2003.*

(Continued)

*Primary Examiner* — Tse Chen
*Assistant Examiner* — Jason Ip
(74) *Attorney, Agent, or Firm* — Squire Patton Boggs (US) LLP

(57) ABSTRACT

A method of treating a cancerous region in a breast of a patient comprising (i) imaging the breast in a three-dimensional coordinate system, (ii) stereotactically determining the location of the cancerous region in the breast, (iii) optionally determining the volume of the entire cancerous region to be treated, and (iv) while maintaining the breast in a three-dimensional coordinate system that is identical to or corresponds with the three-dimensional coordinate system used in (i), noninvasively exposing the cancerous region of the breast of the patient to a cancer-treatment effective dose of radiation; and equipment for use in such a method.

12 Claims, 5 Drawing Sheets

(56) References Cited

U.S. PATENT DOCUMENTS

| | | | |
|---|---|---|---|
| 5,757,886 A | | 5/1998 | Song |
| 5,876,339 A | | 3/1999 | Lemire |
| 5,999,842 A | * | 12/1999 | Harrison et al. .............. 600/474 |
| 6,006,126 A | * | 12/1999 | Cosman ........................ 600/426 |
| 6,463,122 B1 | * | 10/2002 | Moore ............................ 378/65 |
| 6,480,565 B1 | * | 11/2002 | Ning ................................ 378/37 |
| 2006/0262898 A1 | | 11/2006 | Partain et al. |

OTHER PUBLICATIONS

European Search Report application No. EP 08 73 0782 dated Jul. 1, 2010.

Notice of Reasons for Rejection dated Oct. 23, 2012 corresponding to Japanese Patent Application No. 2009-551807 and English translation thereof.

* cited by examiner

Source Aligned with
diameter=2.0 cm

Source Aligned with
diameter=1.5 cm

METHOD AND EQUIPMENT FOR IMAGE-GUIDED STEREOTACTIC RADIOSURGERY OF BREAST CANCER

This invention was made with government support under SBIR Grant Number CA132254 awarded by the National Institutes of Health. The government has certain rights in the invention.

TECHNICAL FIELD OF THE INVENTION

The present invention pertains to magnetic resonance imaging (MRI), radiation, stereotactic radiosurgery, and breast cancer. Specifically, the present invention pertains to a method and equipment employing γ-radiation in image-guided, stereotactic, radiosurgical ablation of a cancerous region in a breast.

BACKGROUND OF THE INVENTION

According to the American Cancer Society, breast cancer is the most prevalent malignancy among women in the United States, with more than 200,000 new cases diagnosed per year (Jemal et al., Cancer J. Clin. 56: 106-130 (2006)). Significant advances have been made in mammography and other imaging modalities over the last few decades. As a result, more patients are diagnosed in the early-stage of the disease, for which breast conservation therapy (BCT) has become the treatment of choice.

Compared with mastectomy, BCT provides a comparable outcome with superior cosmetic results and reduced psychological and emotional trauma (Fisher et al., N. Engl. J. Med. 347(16): 1233-1241 (2002); Veronesi et al., N. Engl. J. Med. 347(16): 1227-1232 (2002); Liljegren et al., J. Clin. Oncol. 17(8): 2326-2333 (2000); Clark et al., J. Natl. Cancer Inst. 88(22): 1659-1664 (1996); and Gray et al., Intl. J. Radiat. Oncol. Biol. Phys. 21: 347-354 (1991)). BCT, however, is a complex, protracted treatment. Patients diagnosed with early-stage breast cancer first undergo a surgical procedure called lumpectomy, in which the tumor and its surrounding tissue, referred to as a margin, are removed. Ideally, a margin of sufficient size is removed so that no tumorous tissue is left behind. However, breast cancer is naturally multi-focal, and, consequently, there are normally small tumor foci scattered around the gross tumor (Holland et al., Cancer 56: 979-990 (1985)). Furthermore, mammograms and magnetic resonance images are obtained under different geometric conditions as compared to surgery, lumpectomy is performed without any direct image guidance, and the geometric uncertainty of surgery is no better than about a centimeter. Therefore, realistically, even though the probability of finding a tumor focus decreases sharply with an increase in distance from the gross tumor (Holli et al., Br. J. Cancer 84(2): 164-169 (2001); Liljegren et al. (2000), supra; and Clark et al. (1996), supra), one or more micro-sized tumor foci are left behind. This is why patients subsequently undergo radiation therapy to treat the surgical margin. If post-operative radiation is not received, about 35% of lumpectomies are expected to fail locally (Early Breast Cancer Trial's Collaborative Group, New Engl. J. Med. 333: 1444-1455 (1995)).

Currently, standard radiation therapy involves irradiation of the whole breast over the course of about 5-7 weeks. Brachytherapy also has been used to treat the surgical margin (Baglan et al., Intl. J. Radiat. Oncol. Biol. Phys. 50(4): 1003-1011 (2001); King et al., Am. J. Surg. 180(4): 299-304 (2000); and Wazer et al., Intl. J. Radiat. Oncol. Biol. Phys. 53(4): 889-897 (2002)), and involves the interstitial introduction of radioactive seeds of high or low activities into the breast. Accelerated partial breast irradiation (APBI), which involves irradiation of the surgical bed of the breast over the course of about 1-2 weeks, is currently being tested in several clinical trials (Vicini et al., J. Clin. Oncol. 19(7): 1993-2001 (2001)).

Unfortunately, external radiation beams, whether employed over 1-2 weeks or 5-7 weeks, can lead to pulmonary (Lingos et al., Intl. J. Radiat. Oncol. Biol. Phys. 21: 355-360 (1991); and Rothwell et al., Radiother. Oncol. 4: 9-14 (1985)) and cardiovascular (Corn et al., J. Clin. Oncol. 8: 741-750 (1990); Dodwell et al., Australasian Radiol. 38: 154-156 (1994); and Rutqvist et al., Intl. J. Radiat. Oncol. Biol. Phys. 22: 887-896 (1992)) damage, skin and soft tissue fibrosis (Johansen et al., British J. Radiol. 67: 1238-1242 (1994)), arm edema (Wallgren, Acta Oncologica 31(2): 237-242 (1992)), and increased risk of secondary cancer (Inskip et al., J. Natl. Cancer Inst. 86(13): 983-988 (1994); and Wallgren (1992), supra). These drawbacks adversely affect the quality of life of patients undergoing BCT.

The improved sensitivity and specificity of three-dimensional MRI (3-D MRI) has challenged surgeons to provide a less invasive, equally effective, and cosmetically superior alternative to a lumpectomy. Consequently, efforts to develop minimally invasive techniques for breast cancer surgery have increased (Dowlatshahi et al., The Amer. J. of Surgery 182: 419-425 (2001)). These efforts include hot (Jeffrey et al., Arch. Surg. 134: 1064-1068 (1999); and Izzo et al., Proc. Am. Soc. Clin. Oncol. 19: 80A (2000)) and cold (Staren et al., Arch. Surg. 132: 28-33 (1997)) percutaneous ablation, and the use of automated needles (Liberman et al., Am. J. Roentgenol. 173: 1315-1322 (1999); and Burak et al., Arch. Surg. 135: 700-703 (2000)), cannulae (D'Angelo et al., Am. J. Surg. 174: 297-302 (1997); Chesbrough et al., Radiology 209: 197 (1999); and Liebman et al., Am. J. Roentgenol. 172: 1409-1412 (1999)), and lasers (Harries et al., Br. J. Surg. 81: 1617-1619 (1994); Mumtaz et al., Radiology 200: 651-658 (1996); Milne et al., Lasers Surg. Med. 26: 67-75 (2000); and Dowlatshahi et al., Breast J. 2: 304-311 (1996)).

One of the more widely tested hot ablative techniques is radiofrequency ablation (RFA) (Jeffrey et al. (1999), supra; and Izzo et al. (2000), supra). Under general anesthesia, the RFA probe is inserted into the tumor under sonographic guidance. The radiofrequency current applied to the electrode causes the temperature near the electrode to rise gradually to a target temperature, e.g., 95° C., over a period of about 5 to 7 minutes. The temperature is then maintained at the target temperature for about 15 minutes, after which it is allowed to cool down for about 1 minute. A cold ablative technique, i.e., cryotherapy, involves circulating liquid nitrogen to the tip of a probe to form an ice ball to destroy cells. Although these ablative methods are meant to be minimally invasive, they have to be performed under general anesthesia. In addition, it is difficult, if not impossible, to conform precisely the damage generated to the shape of the tumor, such that unnecessary damage to surrounding normal tissue is avoided or minimized. These techniques have not been demonstrated to be able to replace surgery.

Due to the precision of image-guided needle biopsy, surgeons have tried to use a vacuum-assisted biopsy technique to remove gross and microscopic tumors piecemeal (Liberman et al. (1999), supra; and Burak et al. (2000), supra), or to use a large-core cannula in conjunction with stereotactic localization to remove a non-fragmented, single, large-core specimen (D'Angelo et al. (1997), supra; Chesbrough et al. (1999), supra; and Liebman et al. (1999), supra). Reported results indicate that complete excision with such techniques appears to correlate better with tumors smaller than about 0.7 cm. Even with small tumors, however, residual tumors are left behind in about 70% of the patients. Therefore, these percutaneous image-guided techniques, though less invasive, cannot replace surgery.

Radiosurgery enables ablation of a tumor with sub-milliliter precision. It has proven to be effective for all sites where a single, high dose can be safely delivered. Most stereotactic radiosurgery has been performed on intracranial tumors using a dedicated device, like the Gamma Knife or a linear accelerator, with multiple arced beams focused at the tumor site. Radiosurgery also has been successfully used for extracranial sites, such as the lung and the spine. Radiosurgery is especially effective for metastatic cancer, e.g., metastatic breast cancer, in the brain. A single dose of about 16-24 Gy to the metastatic tumor eradicates the tumor in more than 85% of the cases (Vesagas et al., J. Neurosurg. 97(5 Suppl.): 507-510 (2002); and Kondziolka et al., Cancer 104(12): 2784-2791 (2005)), although doses of less than 20 Gy are generally delivered with a palliative intent.

To date, the inventors are not aware of anyone who has applied stereotactic radiosurgery to the breast. In this regard, the inventors are not aware of any device that can deliver a high dose of radiation to a cancerous region of the breast safely and accurately with surgical precision. Unlike radiosurgery of intracranial tumors, where the radiation beam can approach the intracranial lesion from more than a $2\pi$ solid angle, the breast can only be approached from limited, unobstructed angles by external radiation beams, such as those generated by a linear accelerator. Furthermore, unlike the skull, which can be securely fixated into a coordinate system so that there is no geometric difference between imaging and treatment, such immobilization has never been achieved with a breast.

In view of the above, it is an object of the present invention to provide a method of using stereotactic radiosurgery to treat a cancerous region in a breast. It is a further object of the present invention to provide equipment for use in the method. These and other objects and advantages, as well as additional inventive features, will become apparent from the detailed description provided herein.

SUMMARY OF THE INVENTION

The present invention provides a method of treating a cancerous region in a breast of a patient. The method comprises (i) imaging the breast in a three-dimensional coordinate system, (ii) stereotactically determining the location of the cancerous region in the breast, (iii) optionally determining the volume of the entire cancerous region or portion thereof to be treated, and (iv) while maintaining the breast in a three-dimensional coordinate system that is identical to or corresponds with the three-dimensional coordinate system used in (i), noninvasively exposing the cancerous region of the breast of the patient to a cancer-treatment effective dose of radiation.

The present invention further provides equipment for image-guided stereotactic radiosurgery of a cancerous region in a breast. The equipment comprises: (i) means for immobilizing the breast containing the cancerous region; (ii) a couch comprising a channel or right and left openings, wherein the right or left breast of a patient is placed in the channel or the right or left opening, respectively, for treatment when the patient is lying prone on the couch, which optionally comprises a top layer of a self-molding medium; (iii) a stereotactic localization frame beneath the couch for placement of the breast in a coordinate system; (iv) one or two breast shields, which are removably attached to the couch, slidably mounted to the channel, or removably attached to the means for immobilizing the breast; (v) an irradiation unit comprising (i') a source holder, which comprises a wall having an interior surface, an exterior surface, and channels, which communicate with the interior surface, may or may not communicate with the exterior surface, and each of which can comprise a radiation source, (ii') a collimator holder, which is adjacent to the interior surface of the source holder and comprises collimators of different sizes in the same arrangement as the channels in the source holder such that relative rotation between the source holder and the collimator holder allows selection of radiation beams of different sizes, resulting in shots of radiation of different sizes, and (iii') a base housing, which is beneath the exterior surface of the source holder, supports the source holder and the collimator holder, and houses a motor, which rotates the collimator holder and the source holder relative to each other, and another motor, which rotates the collimator holder and the source holder together, when locked; (vi) a curved base support; (vii) three motors, which are operably connected to the couch and each of which moves the couch in a different axis of motion; and (viii) a computerized control system, which controls the movement of the couch and the irradiation unit. The equipment can, and preferably does, further comprise a treatment planning system. The operations of the irradiation unit and the couch are controlled by a computerized control system, which obtains treatment parameters from the treatment planning system, controls the movement of the couch and the irradiation unit according to the treatment plan, monitors the safety and operation of the entire unit, and provides safety interlocks and movement limits when needed.

DETAILED DESCRIPTION OF THE INVENTION

Figure 1:
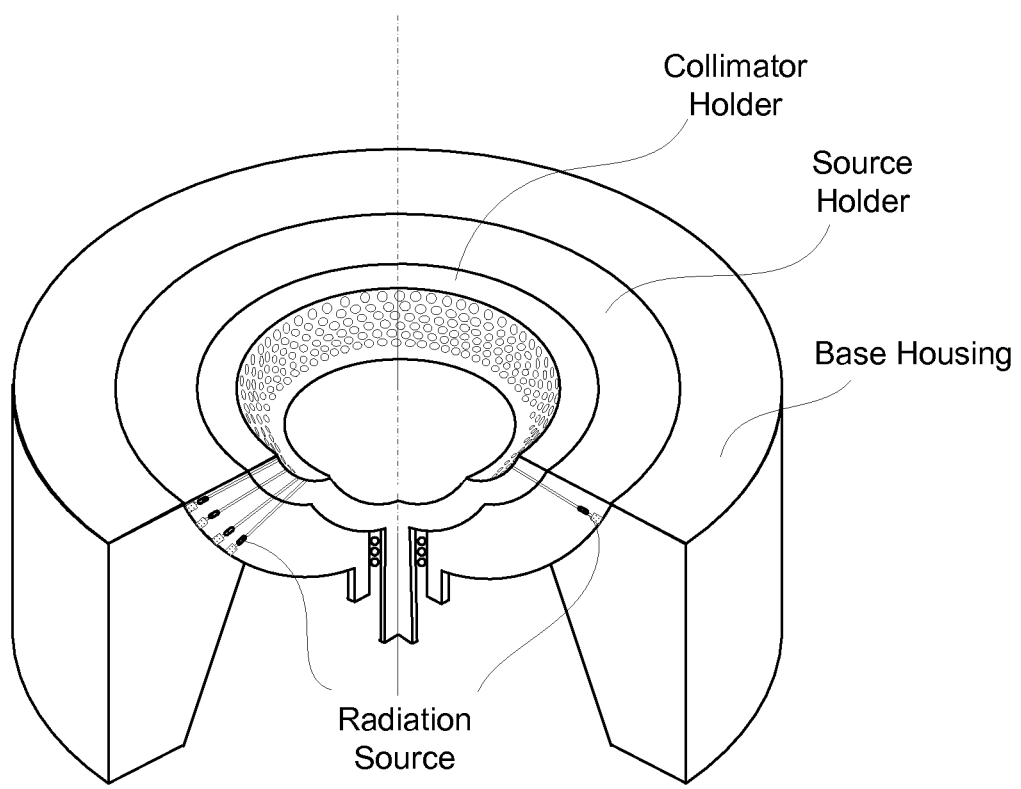
FIG. 1 is a cutout view of the γ-irradiation unit.

The present invention provides a method of using stereotactic radiosurgery to treat a cancerous region of a breast. The present invention also provides equipment for use in the method. The method and equipment of the present invention are believed to offer potential advantages over current methods of treatment, including BCT. The potential advantages include, but are not limited to, non-invasive nature, no pain, potential for elimination of radiation treatment for most, if not all, early-stage breast cancers, enhanced quality of life (by shortening the treatment time from 7-10 weeks to hours), absence of scars, reduced radiation to non-cancerous tissue, ease of repetition, and cost-effectiveness, due to the elimination of invasive surgery and subsequent radiation therapy.

Due to stereotactic localization, it is believed that an accuracy of about 1 mm can be achieved. With breast cancer radiosurgery, a substantial radiation dose is inevitably delivered to the outside of the target volume; however, the dose falls off very quickly with an increase in distance from the target. The high-dose gradient roughly matches that required to sterilize most effectively any residual tumor foci surrounding the gross tumor. At 1 cm from the edge of the target, the dose drops to about 10-15% of the maximum focal dose inside of the tumor. If the minimum dose covering the target is 25 Gy, which is typically 50% of the maximum dose, the dose at 1 cm from the target is 5-7.5 Gy. The natural dose gradient is similar to that of brachytherapy or the MammoSite (Proxima Therapeutics, Inc., Alpharetta, Ga.). Thus, in distinct contrast to radiosurgery of intracranial lesions, the dose outside of the target is useful and desirable for sterilizing potential tumor foci outside of the high dose target. It is this feature that allows for the elimination of post-operative radiation therapy.

In view of the above, the present invention provides a method of treating a cancerous region in a breast of a patient. The method comprises (i) imaging the breast in a three-dimensional coordinate system, (ii) stereotactically determining the location of the cancerous region in the breast, (iii) optionally determining the volume of the entire cancerous region or portion thereof to be treated, and (iv) while maintaining the breast in a three-dimensional coordinate system that is identical to or corresponds with the three-dimensional coordinate system used in (i), noninvasively exposing the cancerous region of the breast of the patient to a cancer-treatment effective dose of radiation.

The entire breast must be located within the same (or corresponding) three-dimensional coordinate system used during imaging and radiosurgery. In addition, the shape and location of the breast within the three-dimensional coordinate system must be identical (or correspond) during imaging and radiosurgery. The present invention further provides a means to immobilize the breast, such as a breast cup (as described below), and a stereotactic localization frame around the cup to establish a coordinate system with respect to the cup.

A computerized treatment planning system identifies the images of the stereotactic localization frame, which appears as dots in the cross-sectional breast images, calculates the location and orientation of the imaged slice, and plans every point on the image accurately in the coordinate system. Contouring tools can be used to determine the volume of the entire cancerous region or portion thereof to be treated. The computerized treatment planning system also allows manual placement of radiation centers of different collimator sizes (i.e., "shots") onto the cancerous region, and will automatically optimize the sizes and locations of the shots. After the treatment is designed, the treatment parameters understandable by the control system of the irradiation unit are electronically sent to the control system of the irradiation unit for treatment delivery. Such planning methods are currently being used in the treatment of intracranial lesions (Shepard et al., Int'l J. of Radiat. Oncol. Biol. Physics 56(5): 1488-1494 (2003); and Yu et al., Tech. in Cancer Res. and Treatment 2(2): 93-104 (2003)).

Any suitable radiation source, such as a radioisotope, which has a half-life of appropriate length for the treatment of cancer and which can deliver a treatment-effective dose of radiation to a depth of 10 cm or more, such as γ-radiation, can be used. A half-life longer than about 12 months is desirable, although a shorter half-life isotope with otherwise desirable characteristics also can be considered. A treatment-effective dose is about 20 Gy to about 60 Gy. An example of a suitable radioisotope is Cobalt 60 ($^{60}$Co), which has a half-life of about 5.3 years and which can generate a treatment-effective dose of γ-radiation with mean photon energy of 1.25 MeV. Alternatively, small x-ray sources, either from an x-ray tube or an x-band linear accelerator, can be used. The cancer treatment-effective dose of radiation can be delivered in one treatment session or in a number of repeated sessions.

In view of the above, the present invention further provides equipment for use in the method of treating a cancerous region in a breast of a patient. The equipment comprises: (i) means for immobilizing the breast containing the cancerous region; (ii) a couch comprising a channel or right and left openings, wherein the right or left breast of a patient is placed in the channel or the right or left opening, respectively, for treatment when the patient is lying prone on the couch, which optionally comprises a top layer of a self-molding medium; (iii) a stereotactic localization frame beneath the couch for placement of the breast in a coordinate system; (iv) one or two breast shields, which are removably attached to the couch, slidably mounted to the channel, or removably attached to the means for immobilizing the breast; (v) an irradiation unit, such as a γ-ray irradiation unit, comprising (i') a source holder, which comprises a wall having an interior surface, an exterior surface, and channels, which communicate with the interior surface, may or may not communicate with the exterior surface, and each of which can comprise a radiation source, (ii') a collimator holder, which is adjacent to the interior surface of the source holder and comprises collimators of different sizes in the same arrangement as the channels in the source holder such that relative rotation between the source holder and the collimator holder allows selection of radiation beams of different sizes, resulting in shots of radiation of different sizes, and (iii') a base housing, which is beneath the exterior surface of the source holder, supports the source holder and the collimator holder, and houses a motor, which rotates the collimator holder and the source holder relative to each other, and another motor, which rotates the collimator holder and the source holder together, when locked; (vi) a curved base support; (vii) three motors, which are operably connected to the couch and each of which moves the couch in a different axis of motion (see FIG. 1); and (viii) a computerized control system, which controls the movement of the couch and the irradiation unit. The equipment can, and preferably does, further comprise a treatment planning system.

Figure 4A:
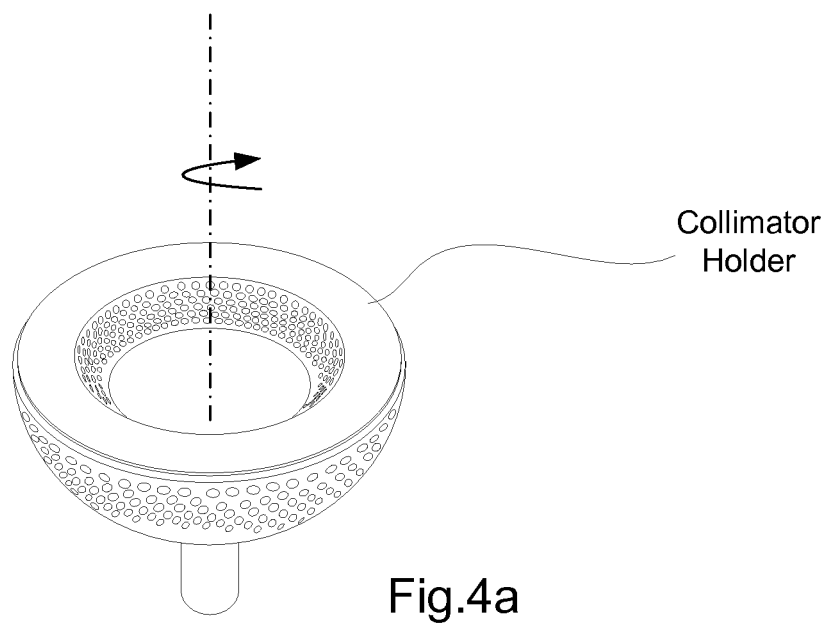
FIG. 4a-FIG. 4b respectively show the source holder and the collimator holder separated from each other.
Figure 4B:
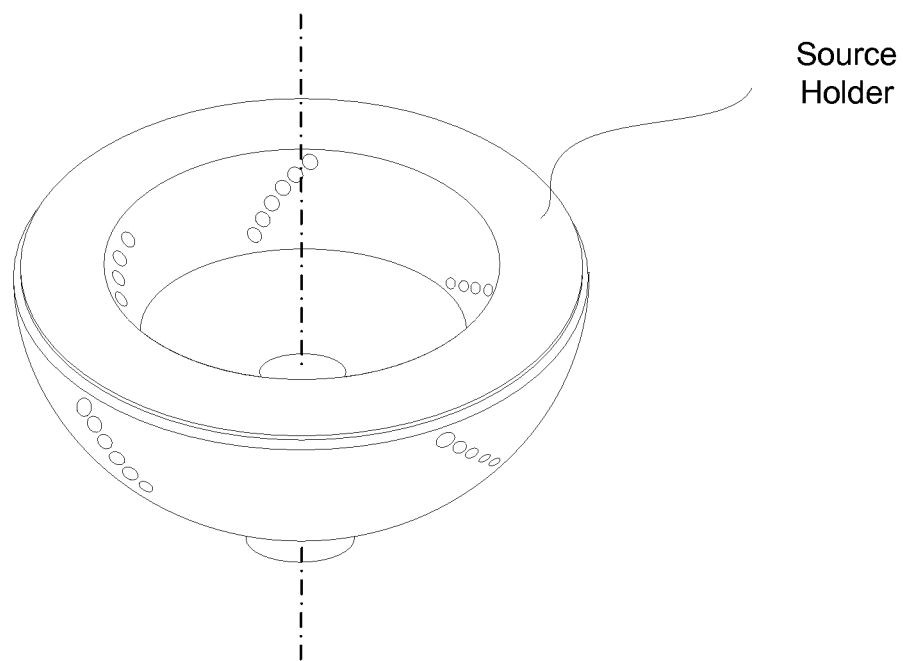

The source holder is preferably bowl-shaped (see FIG. 4b). The lower section of the source holder does not have to follow the same spherical curve as the upper section (see FIG. 1), thereby enabling a deeper treatment space. The source holder desirably is made from a material (e.g., metal) and of sufficient thickness (e.g., from about 10 cm to about 30 cm, depending on the material) to attenuate radiation effectively and to block lateral radiation from the channels (described below). For example, if $^{60}$Co is used as a source of radiation, the source holder preferably is made from cast iron.

Channels are introduced into the wall of the source holder. Each channel has a unique latitude. The channels can be open on the interior surface of the source holder but not on the exterior surface of the source holder. Alternatively, the channels can be open on the interior and exterior surfaces of the source holder, and seals, such as stainless steel screws alone or in further combination with lead plugs, can be used to seal the outer ends of the channels, which open on the exterior surface of the source holder. The radiation source, i.e., radioisotope, is placed into the channels. Desirably, the radioisotope is initially placed in a container, such as a vial, which has a window on the end facing the interior of the source holder, and the vial is then placed in the channel. Cobalt 60, for example, is commercially available from MDS Nordion, Inc. (Ottawa, Canada) as pellets of about 1.2 mm in diameter and about 1 mm in thickness. A number of pellets can be stacked in a vial up to a height of about 2 cm. Preferably, each source vial contains several hundred curies (Ci) of $^{60}$Co, and each source vial is double-encapsulated in a stainless steel housing. Preferably, at least about 30-40 channels are arranged in the wall of the source holder. Any suitable arrangement, which is generally in the top third of the source holder, such as from about −1 degrees to about 35 degrees, can be used, provided that the channels are non-coplanar when the source holder rotates. In this regard, the bottom portion of the source holder, where no source vials are present, can be cut off. The beams emitted from the radiation sources are pointed to a common isocenter on the plane close to the rim of the holder on the central axis of the source holder. When the source holder is rotated, the beams from all of the radiation sources that are present are non-coplanar and focused on the isocenter at all times. Preferably, the total initial activity at the time of installation of the source vials is in the range of about 6,000-10,000 Ci, giving an initial dose rate of 3-4 Gy/min.

A collimator holder containing different sizes of collimator holes is used to select the size of the beam of radiation (see FIG. 4a). The collimator holder is also preferably bowl-shaped but smaller in size (e.g., with an internal diameter that will accommodate a breast with a breast cup, such as about 30 cm or so) such that it can fit concentrically inside of the source holder with a separation of less than about 1 mm (see FIG. 1). If the lower section of the source holder does not follow the same spherical curve as the upper section, then the lower section of the collimator holder should be adjusted accordingly (see, e.g., FIG. 1). The collimator holder and the source holder are concentrically arranged and share the same rotational axis. They are held in their respective positions by separate shafts and bearings. The collimator holder desirably is made from a material and of sufficient thickness (e.g., from about 10 cm to about 30 cm, depending on the material) to block more than about 98% of the radiation outside of the collimator holder. If $^{60}$Co is used as source of the beam, the collimator holder preferably is made from cast iron or tungsten. If the collimator holder is made from tungsten, it can be less thick. If the collimator holder is made from cast iron, tungsten collimators can be inserted into the collimator holder. The latter collimator holder may be less costly and easier to machine. The collimator holder and the source holder are oriented so that both are facing upwards. On the collimator holder are from about 120 to about 200 collimators made from a high density materials, such as tungsten, which vary in size from about 1 cm to about 4 cm projected to the isocenter. The interior surface of the collimator holder can be protected with a thin, replaceable liner, such as a plastic liner.

Figure 5A:
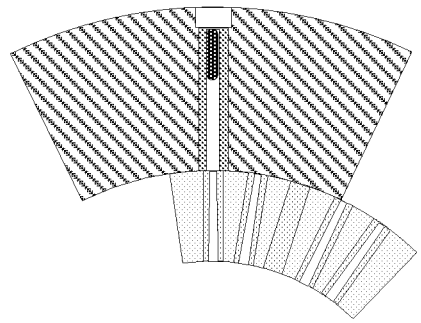
FIG. 5a-FIG. 5c illustrate collimator indexing by a relative rotation between the source holder and the collimator holder (FIGS. 5a and 5b). When the radiation unit is not used for treating patient, the sources are aligned with the solid block on the collimator holder (FIG. 5c).
Figure 5B:
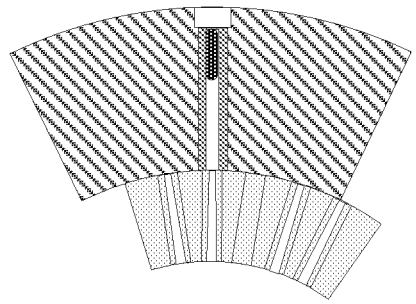
Figure 5C:
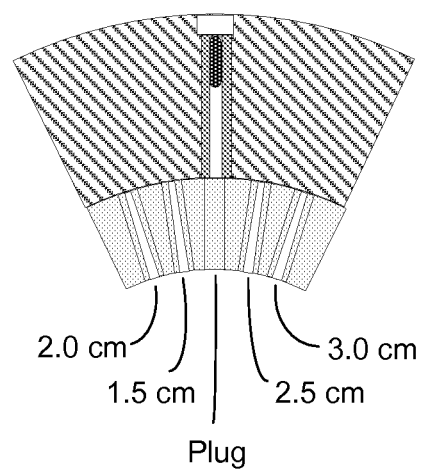

The channels in the source holder always align with solid shielding blocks in the collimator holder when the equipment is not in use in order to shield the release of radiation from the channels. When a breast with a cancerous region is place in the center of the radiation beams by movement of the couch, the required collimator size will be aligned with the radiation source by relative rotation of the source holder and the collimator holder. This enables the radiation sources to be aligned with a specific size of collimator. This process is often called collimator indexing (see FIGS. 5a-5c). During collimator indexing, the sources may have to pass by other collimator holes in order to reach the desired collimator size. In order to avoid radiation from treating outside of the target, the order of rotation and the arrangement of collimator sizes are such that source vials are aligned with collimators from the smallest to the largest and then with a solid section of the collimator holder, which acts as a shield. The order is reversed when the treatment is finished, and the sources are realigned with the solid blocking positions of the collimator holder. If the equipment is used as described herein, the level of radiation leakage is less than that recommended by the National Council on Radiation Protection and Measurements (NCRPM) guidelines (see, e.g., NCRPM Reports No. 49 (1976) and No. 51 (1977)).

Once the source vials in the source holder are aligned with the holes in the desired collimator, the source holder and the collimator holder are locked together with a locking means, such as tapered locking pins driven by solenoids. Once the source holder and the collimator holder are locked together, they rotate about the central axis together. The beams of radiation from the source vials form arcs focused on the isocenter, i.e., the focal spot of all radiation beams. Since the channels containing the source vials are non-coplanar, all of the beams are non-coplanar. The arcs provide a focal dose of about one hundred times greater than the dose delivered to the skin of the breast.

One of ordinary skill in the art will appreciate that different configurations of source holder and collimator holder are possible. In this regard, a large number, e.g., more than about 100, sources of radiation could be used, in which case the source holder and the collimator holder would not have to rotate relative to each other to achieve the desired dose ratio between the isocenter, where the cancerous region of the breast is placed, and the other regions of the breast. The source holder and the collimator holder also do not have to be bowl-shaped. Rather, each channel has a unique combination of latitude and longitude, and the beams from all of the radiation sources are focused on an isocenter at all times.

Figure 3:
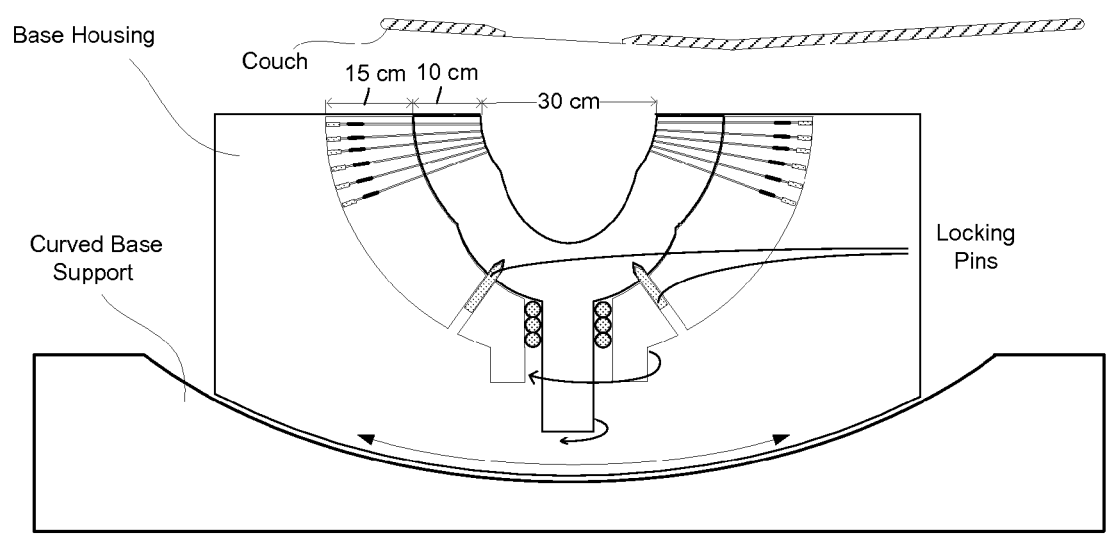
FIG. 3 is a transverse view of the γ-irradiation unit, including possible dimensions.

Beneath the source holder is a base housing (see FIG. 1). The base housing supports the source holder and the collimator holder, attenuates any radiation leakage from the source vials, and houses a motor, which rotates the collimator holder and the source holder relative to each other, and another motor, which rotates the collimator holder and the source holder together, when locked. Another motor can sway the entire radiation unit, including the base, sideways about the radiation isocenter, so that the surface plane of the collimator can best conform to the contour of the patient's chest wall. Preferably, the base housing attenuates any radiation leakage to less than about 2.0 mR/hr at 1 meter from the unit in any direction when the source vials are freshly installed. This requires the thickness of the shielding to be five times the tenth value layer (TVL). Preferably, the shielding in the base housing comprises lead or a lead alloy. For example, an 18 cm thick layer of lead would be sufficient to shield the $^{60}$Co source vials. The base housing is preferably mounted on a curved base support (see FIG. 3), such as one comprising curved tracks with their axes of rotation through the isocenter, such that the irradiation bowl can sway (e.g., +/−30°) in the transverse plane in addition to x, y and z translations of the patient treatment couch, which is described below. The center of the curvature of the base is also the focus of the radiation beams. This enables cancerous regions in the outer quadrants of the breast to be aligned with the isocenter.

Figure 2:
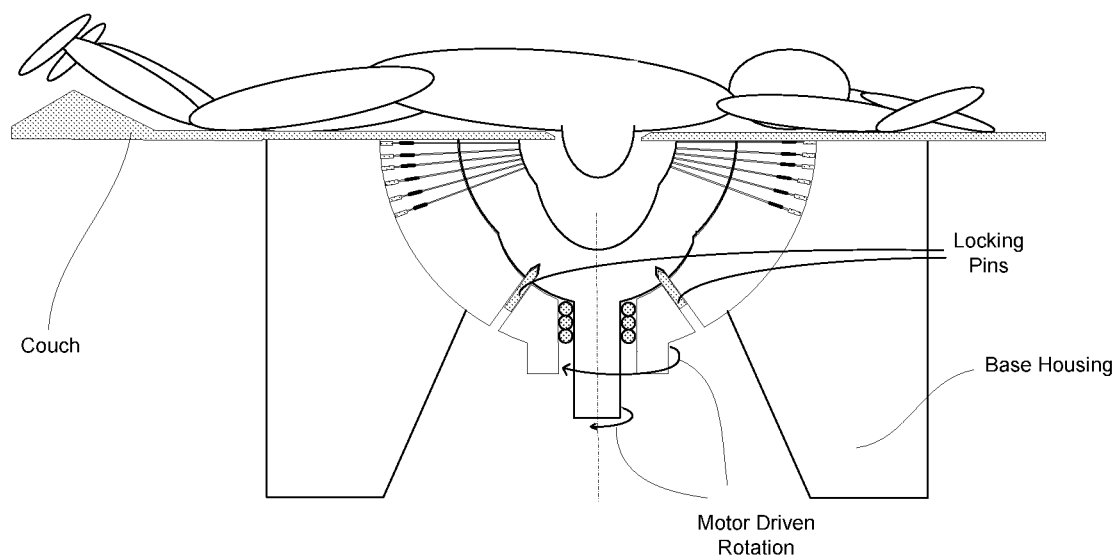
FIG. 2 is a sagittal view of the γ-irradiation unit.

The couch (see FIG. 2) comprises a channel or left and right openings, wherein the right or left breast is placed in the channel or the right or left opening, respectively, for treatment when the patient is lying prone on the couch. The length of the couch should be sufficient to accommodate women as short as about 4' 10" to as tall as about 6' 6". The width of the couch can vary somewhat along its length. The surface of the couch comprises a radiation shield, such as a layer of lead sandwiched between two layers of stainless steel or other material, such as plastic and carbon fiber. If desired, the surface of the couch can further comprise a top layer of a self-molding medium so as to provide a custom fit for the patient, thereby stabilizing the patient during treatment. For example, the couch could be covered with a vacuum bag filled with Styrofoam beads. The patient could lie on the vacuum bag, when the contents are not under vacuum, and adopt a comfortable position. A vacuum could then be applied to the contents to maintain the contours generated in the beads by the patient's body.

When one breast is being treated, the other breast is shielded from radiation. Therefore, if the couch comprises a channel opening through which the breast is placed, the couch further comprises one or two breast shields, which may be removably attached to the couch or slidably mounted to the channel of the couch. Alternatively, a separate breast shield can be removably attached to each of the breast cups, which are described below. If the breast shields are attached to the patient treatment couch, the couch further comprises means for attachment, such as locking holes, which mate with attachment means on the breast shields. If one or two breast shields are slidably mounted to the channel of the couch, the couch further comprises a means of engaging the edge of the shield(s) so that it/they can be slid from one position to another. When the equipment is not in operation, the channel or two openings on the couch can be blocked with the breast shields or the solid portion of the couch can be driven to cover the bowls of the collimator holder and the source holder to provide additional shielding from radiation.

The position of the couch is driven by three motors, such as analog or digital motors, so that movement in three axes of motion can be achieved. Redundant positional sensors are used to ensure positional accuracy. Preferably, the couch is configured to reduce back strain. For example, the portion of the couch supporting the lower body can be lowered, thereby reducing strain on the lower back. Preferably, the couch is also configured to allow the arms to rest on either side of the head, preferably with elbows bent, so as to maximize exposure of the outer quadrants of the breast and to avoid exposing the arms to radiation. The lower portion of the couch also can be designed to allow the contralateral leg to be at a retracted position to reduce the pressure of the contralateral breast and improve patient comfort.

In view of the above, the present invention provides a method of using the equipment to treat a cancerous region in a breast of a patient. As indicated above, the entire breast must be located within the same (or corresponding) three-dimensional coordinate system used during imaging and radiosurgery. In addition, the shape and location of the breast within the three-dimensional coordinate system must be identical (or correspond) during imaging and radiosurgery.

First, the breast is preferably immobilized. Any suitable method of immobilization can be used. A preferred method involves the use of a thermoplastic, which is soft and expandable upon heating and which hardens upon cooling to room temperature. Preformed thermoplastic breast cups of varying size and fixed thickness can be used. Prior to applying the preformed cup to the patient, the patient lays down prone on the couch with her breasts in the channel or openings. The heated thermoplastic is then molded to fit the patient's breast. Once the breast cups have hardened by cooling to room temperature, the breast cups are fitted with a comfortable rim, such as a flat rubber rim, by means of an adhesive, such as a wax tape-protected ring of glue, similar to that which is used under an EKG probe, for effective fixation to the skin of the chest wall. The breast cups can be further secured by a band or strap around the patient's chest. On the outer side of the rim are means for attaching the breast cups to the couch. For example, locking pins can be attached to the outer side of the rim and can engage locking holes on the couch. Preferably, the inside of the breast cup is coated with a layer of tacky adhesive, such as a thin layer of sticky glue or artist's glue, to fix the contact between the patient's skin and the breast cup. Since the rim of the breast cup is taped onto the skin of the patient's chest wall, relative movement of skin and the thoracic rib cage may cause minor changes of tissue position inside of the cup. In order to prevent that from happening, the position of the breast cup relative to the rib cage should be maintained. Once vacuumed, the vacuum bag containing Styrofoam beads on top of the couch will enable consistent and reliable set-up of the patient during imaging and irradiation. In this regard, the vacuum bag and the surface of the couch are indexed so that the vacuum bag will fit the surface of the couch during imaging and radiation the same way. If the breast is not immobilized, markers can be implanted and imaged, or the surface of the breast can be 3-dimensionally imaged and deformable images can be registered.

In order to image the breast in a three-dimensional coordinate system, a stereotactic localization frame is located underneath the couch and can be, for example, affixed to the bottom of the couch around the channel or openings for the breasts, attached to the breast cup, or be part of the breast cup. The stereotactic localization frame can be of any suitable shape, such as cylindrical or rectangular, with horizontal and diagonal rods containing tubes filled with MRI-enhancing solution, which shows up as bright lines in MRI images. In a preferred embodiment, there will be tubes placed at the base of the breast cup and additional tubes placed at an angle to the base tubes. The localization frame has a fixed geometric relationship with the channel or openings in the couch and the breast (or breast cup). After the images are obtained, there will be at least three bright dots on each image slice, indicating the locations of the rods at the base of the breast cup and the angled rods. In this manner, the image is precisely placed in the coordinate system defined by the localization frame. Alternatively, a spiral wire can be mounted on the underside of the couch or the breast cup with the diameter of the helix not smaller than the diameter of the opening or the width of the channel so that the helix encircles the breast. MRI-enhancing solution is sealed inside of the hollow wire. Since the geometry of the helix is known, the data shown on each slice of the MRI image will uniquely place the slice in the coordinate system.

The errors in identifying the location of the cross-sectional image of the rods of the stereotactic frame, which appear as bright dots on the cross-sectional image of the breast, will be translated to the geometric error of the treatment. To minimize such geometric error, a least-square regression algorithm is employed by the treatment planning computer to maximize consistency between the images of the stereotactic frame and the known geometry of the stereotactic frame. With this method, errors made on an individual dot, or made on one image slice, will not affect the overall accuracy.

The couch used for imaging is identical to the couch used for irradiation in surface shape and the location and the shape of the channel or openings for the breasts; however, they are made of different materials and are supported differently. The imaging couch is just a shell that fits on the breast coil, which can be part of a dedicated breast imaging couch or a couch-top unit. The imaging couch needs to be adapted to fit on MRI from different vendors. The coordinates defined by the imaging localization frame are transferable to the patient treatment couch. If desired, the MRI images can be used to determine the volume of the entire cancerous region or portion thereof to be treated.

The operations of the irradiation unit and the couch are controlled by a computer control system, which obtains treatment parameters from the treatment planning system, controls the movement of the couch and the irradiation unit according to the treatment plan, monitors the safety and operation of the entire unit, and provides safety interlocks and movement limits when needed.

Once the contour of the breast is determined from the MRI images, the traveling ranges of all three axes of the couch are automatically calculated to form an envelope of motion to avoid collisions of the inner surface of the collimator holder with the breast cup. The isocenter of the radiation beam is used as an origin for the coordinates of the movement of the couch. When the breast, such as a breast in a breast cup, is immobilized, the breast is accurately placed in the coordinate system. Then the isocenter is aligned with the location in the cancerous region of the breast of the patient to be irradiated. The correct size collimator is selected by rotating the collimator holder relative to the source holder and aligning the correctly sized collimator holes with the channels in the source holder containing the radiation sources. Once the desired alignment is achieved, the collimator holder and the source holder are then locked together. After the specified treatment time, the source holder and the collimator holder are unlocked, and the collimator holder and the source holder are rotated relative to each other until the source vials are shielded.

In view of the above, a dedicated treatment planning system, which designs the focal size and location based on the 3-D MRI images, is needed. The system, which models the γ-radiation precisely, comprises a computer, supporting circuitry, and various software modules including, but not limited to, DICOM import images, stereotactic localization involving the use of a linear regression operation at the end to minimize geometric error made on each slide in identifying the locations of the rods of the localization frame, target delineation (optional) involving the use of contouring tools to delineate the gross tumor and/or the intended treatment volume so as to optimize shots of radiation and dose-volume analysis, shot placement to determine the location, size and weightings of the shots to use to fit best the shape of the cancerous region, dose calculation in real-time for display on the MRI image, dose display of the final dose in Gy, and printing of 2-D and 3-D dose displays and a plan summary. The treatment planning system can analyze the treatment plan using commonly accepted metrics in the field of radiation therapy, such as volume histograms and conformity indices. If desired, the shots can be administered manually by an operator of the equipment. The dose displays can be printed along with a treatment plan summary, which can include, for example, the treatment time at each focal spot, the coordinates of the couch for each focal spot, and the sway angle of the irradiation unit.

All references, including publications, patent applications, and patents, cited herein are hereby incorporated by reference to the same extent as if each reference were individually and specifically indicated to be incorporated by reference and were set forth in its entirety herein.

The use of the terms "a," "an," "the," and similar referents in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to illuminate better the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. It should be understood that the illustrated embodiments are exemplary only, and should not be taken as limiting the scope of the invention.

What is claimed is:

1. An equipment for image-guided stereotactic radiosurgery of a cancerous region in a breast, which equipment comprises:
   (i) means for immobilizing the breast containing the cancerous region, the means including a breast cup;
   (ii) a couch comprising a channel or right and left openings, wherein the right breast or the left breast of a patient is placed in the channel or the right or left opening, respectively, for treatment when the patient is lying prone on the couch, which comprises a top layer of a self-molding medium;
   (iii) a stereotactic localization frame beneath the couch for placement of the breast in a coordinate system;
   (iv) one or two breast shields, which are removably attached to the couch, slidably mounted to the channel, or removably attached to the means for immobilizing the breast;
   (v) an irradiation unit comprising (i') a source holder, which comprises a wall having an interior surface, an exterior surface, and channels, which communicate with the interior surface and the exterior surface, and each of which comprises at least one of x-ray radiation sources or gamma radiation sources, (ii') a collimator holder, which is adjacent to the interior surface of the source holder and comprises collimators of different sizes in the same arrangement as the channels in the source holder such that relative rotation between the source holder and collimator holder allows selection of radiation beams of different sizes, resulting in shots of radiation of different sizes, and (iii') a base housing, which is beneath the exterior surface of the source holder, supports the source holder and the collimator holder, and houses a motor, which rotates the collimator holder and the source holder relative to each other, and another motor, which rotates the collimator holder and the source holder together, when locked;
   (vi) a curved base support, wherein the curved base support is configured with a center of curvature which coincides with the focus of the radiation beams and wherein the curved based support is configured to translate motion of an axis of rotation of the base housing, the source holder, and the collimator holder;
   (vii) three motors, which are operably connected to the couch and each of which moves the couch in a different axis of motion; and
   (viii) a computerized control system, which controls the movement of the couch and the irradiation unit.

2. The equipment of claim 1, wherein each channel has a unique latitude and, when the source holder is rotated, the beams from all of the radiation sources that are present are non-coplanar and focused on an isocenter at all times.

3. The equipment of claim 1, wherein the source holder comprises more than 100 channels, each of which comprises a radiation source and has a unique combination of latitude and longitude, and the beams from all of the radiation sources are focused on an isocenter at all times.

4. The equipment of claim 1, wherein the collimator holder further comprises solid shielding blocks for alignment with the channels to shield the release of radiation from the channels when the equipment is not in use.

5. The equipment of claim 1, wherein the couch in (ii) is identical to that which is used in imaging.

6. The equipment of claim 1, which further comprises a treatment planning system.

7. The equipment of claim 6, wherein a least-square regression algorithm is used to maximize the consistency between the images of the stereotactic frame and the known geometry of the stereotactic frame.

8. The equipment of claim 6, wherein the treatment planning system places the images of the breast in the coordinate system, thereby allowing the localization of the cancerous regions of the breast.

9. The equipment of claim 6, wherein the computer automatically places shots of radiation of appropriate size and strength at optimal locations in the cancerous region of the breast.

10. The equipment of claim 6, wherein an operator of the equipment places shots of radiation of appropriate size and strength at optimal locations in the cancerous region of the breast.

11. The equipment of claim 6, which the treatment planning system displays the dose(s) of radiation on an MRI image and analyzes the treatment plan.

12. The equipment of claim 11, which prints the dose displays and a treatment plan summary.

* * * * *